United States Patent

Izuchukwu et al.

[19]

[11] Patent Number: 5,938,101
[45] Date of Patent: *Aug. 17, 1999

[54] SKIN STAPLER WITH MOVABLE ANVIL

[75] Inventors: John I. Izuchukwu, Loveland, Ohio; John J. Mertz, Ludlow, Ky.; Richard R. Schweet; Jeremy D. Jarrett, both of Cincinnati, Ohio; Charles A. Hansford, Liberty Township, Ohio

[73] Assignee: Ethicon Endo-Surgery, Inc., Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/856,061

[22] Filed: May 14, 1997

[51] Int. Cl.$^6$ .................................................. A61B 17/064
[52] U.S. Cl. ........................... 227/176.1; 227/83; 227/88; 227/19
[58] Field of Search ................................. 227/83, 88, 89, 227/19, 175.1, 176.1

[56] References Cited

U.S. PATENT DOCUMENTS

| | | | |
|---|---|---|---|
| 3,643,851 | 2/1972 | Green et al. | 227/19 |
| 4,109,844 | 8/1978 | Becht | 227/120 |
| 4,127,227 | 11/1978 | Green | 227/83 |
| 4,179,057 | 12/1979 | Becht et al. | 227/19 |
| 4,196,836 | 4/1980 | Becht | 227/110 |
| 4,391,402 | 7/1983 | Campbell et al. | 227/19 |
| 4,406,392 | 9/1983 | Campbell et al. | 227/19 |
| 4,410,125 | 10/1983 | Noiles et al. | 227/19 |
| 4,411,378 | 10/1983 | Warman | 227/19 |
| 4,493,322 | 1/1985 | Becht | 128/334 |
| 4,523,707 | 6/1985 | Blake, III et al. | 227/19 |
| 4,558,810 | 12/1985 | Mulhauser et al. | 227/88 |
| 4,591,086 | 5/1986 | Campbell et al. | 227/19 |
| 4,596,350 | 6/1986 | Smith et al. | 227/19 |
| 4,648,542 | 3/1987 | Fox et al. | 227/19 |
| 4,664,305 | 5/1987 | Blake, III et al. | 227/19 |
| 4,691,853 | 9/1987 | Storace | 227/19 |
| 4,747,531 | 5/1988 | Brinkerhoff et al. | 227/19 |
| 4,796,793 | 1/1989 | Smith et al. | 227/19 |
| 4,807,628 | 2/1989 | Peters et al. | 227/19 |
| 4,811,886 | 3/1989 | Murray | 227/19 |
| 4,887,756 | 12/1989 | Puchy | 228/88 |
| 4,951,860 | 8/1990 | Peters et al. | 227/177 |
| 5,161,725 | 11/1992 | Murray et al. | 227/182 |
| 5,170,926 | 12/1992 | Ruckdeschel et al. | 227/177 |
| 5,240,164 | 8/1993 | Murray et al. | 227/175 |
| 5,251,801 | 10/1993 | Ruckdeschel et al. | 227/177 |
| 5,330,087 | 7/1994 | Murray et al. | 227/175 |
| 5,376,095 | 12/1994 | Ortiz | 606/143 |

FOREIGN PATENT DOCUMENTS

84/01706  5/1984  WIPO .............................. 227/176.1

*Primary Examiner*—Lee Young
*Assistant Examiner*—A. Dexter Tugbang
*Attorney, Agent, or Firm*—Louis J. Capezzuto

[57] ABSTRACT

An improved surgical stapler which allows for the multi-directional release of staples includes a stapler body and a driver contained therein. A magazine is connected to the stapler body and includes a plurality of staples. The magazine also includes an anvil having a staple forming surface at a distal end thereof for forming a staple thereon. The anvil is movable from a staple forming position to a staple release position. A feeder element which is spring biased against the staples is used for feeding each staple to the staple forming surface. A trigger is operatively connected to the driver and is movable from a pre-fire position to a firing position for advancing the driver against the anvil for forming the staple against the staple forming surface of the anvil. The trigger is operatively connected to the anvil for moving the anvil from the staple forming position to the staple release position for releasing the staple from the stapler.

9 Claims, 6 Drawing Sheets

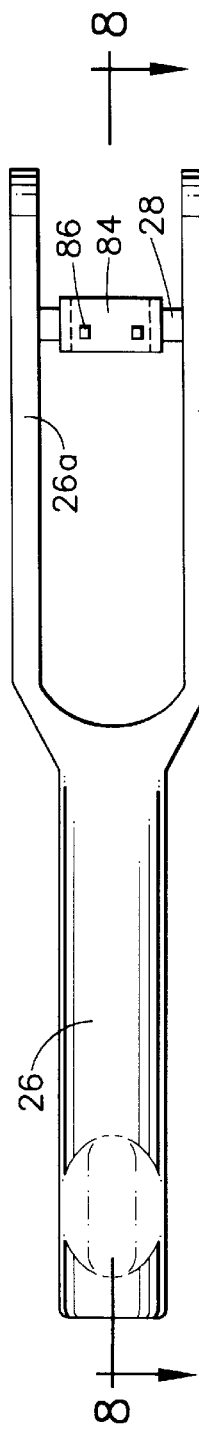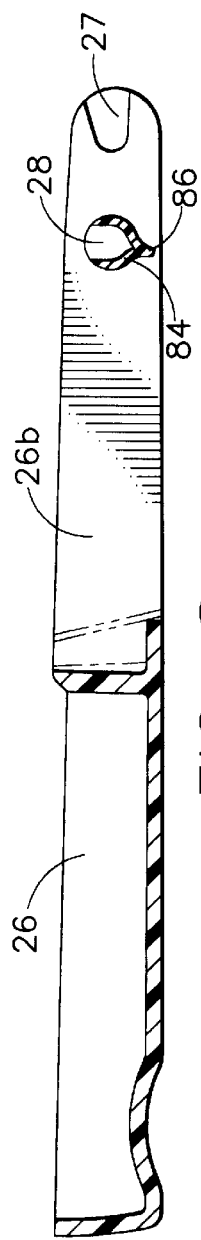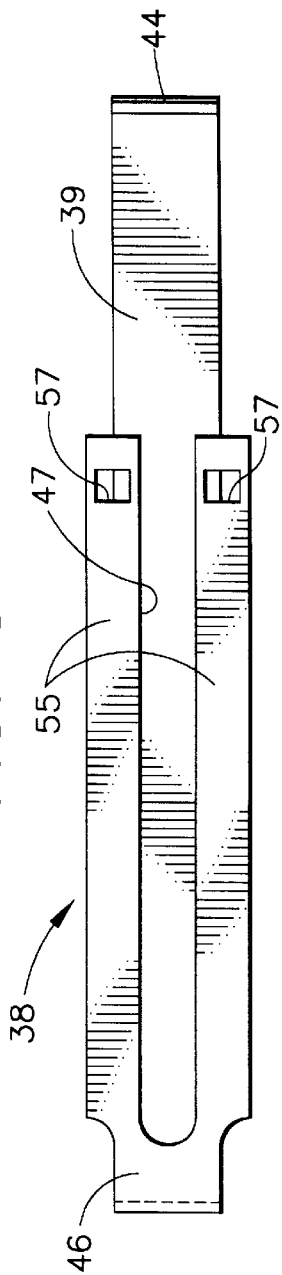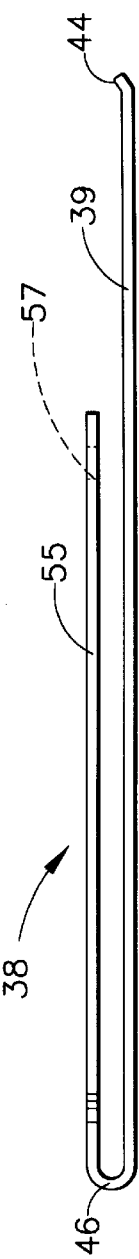
FIG. 7
FIG. 8
FIG. 9
FIG. 10

SKIN STAPLER WITH MOVABLE ANVIL

FIELD AND BACKGROUND OF THE INVENTION

The present invention relates, in general, to tissue fastening devices and, in particular, to a new and useful wound closure device, such as a skin stapler, that utilizes a movable anvil that allows for the multi-directional release of a staple from the device upon firing.

It is well established in the prior art that there are many devices that exist which utilize staples for fastening tissue. Many of these existing or known devices are directed toward closing a wound, fastening a skin incision, curing a defect in tissue or fastening a prosthetic to tissue for repairing a defect or the like.

In particular, there are a number of known prior art skin staplers that contain a multiplicity of staples and are used for closing wounds or incisions in the skin. These skin staplers are usually multi-fire instruments meaning that they contain and fire a plurality of staples. These instruments are designed to be disposable and used for a single patient only.

One known prior art skin stapler is disclosed in U.S. Pat. Nos. 4,391,402; 4,406,392 and 4,591,086 (Campbell et al.). Similar to many other known skin staplers, the stapler disclosed in the above-identified patents utilities an L-shaped anvil. The L-shaped anvil configuration comprises an elongated leg portion and a small leg portion that is orthogonal or parallel to the elongated leg portion for providing a staple forming surface thereon. Accordingly, a former or driver is used to move parallel to the elongated leg portion in order to form a staple around the small leg portion of the anvil. In conjunction with the driver and anvil configuration and orientation, a leaf spring, which is a unitary part of the staple track, is utilized for retaining the staple stack away from the staple being formed, e.g. the distal-most staple, on the small leg portion of the anvil in order to prevent the staple stack from interfering with the forming of the distal-most staple.

Other known skin staplers are disclosed in U.S. Pat. No. 3,643,851 (Green et al.) and U.S. Pat. No. 4,127,227 (Green). Similar to the prior art devices described above, these skin staplers utilize a similar anvil having a substantially L-shaped configuration. Additionally, the driver for these stapling instruments is advanced parallel to the elongated leg portion of the anvil. Additionally, a spring ejector is located adjacent the anvil for engaging the formed staple at the crown of the staple in order to lift the staple off of the anvil by its crown after firing.

In addition to the skin staplers identified above, there are other known skin staplers which also utilize a spring ejector for ensuring that the formed staple is moved away from the anvil of the instrument. These devices are identified as follows: the PRECISE PGX™, manufactured and sold by 3M Healthcare, St. Paul, Minn.; the Davis-Geck APPOSE ULC™, manufactured and sold by American Cyanamid Company, Danbury, Conn.; VISISTAT RH™, manufactured and sold by Edward Weck and Company, Inc., Research Triangle Park, N.C.; and the Auto Suture (Cricket™, Royal™, Signet™, Concorde™, Elite™ and Multi-fire Premium™) skin stapler products, manufactured and sold by United States Surgical Corporation, Norwalk, Conn. All of these skin stapler products are available in the market and utilize a similar driver and anvil configuration such as disclosed above. These devices all utilize a driver that moves substantially parallel to the elongated leg portion of the anvil in order to form a staple across the surface of the small leg portion of the anvil. Furthermore, in all of these skin stapler devices, the staple is moved away from the anvil of the instrument through the use of a spring ejector which engages the staple at the far corners of the staple crown, i.e. at the juncture of the upper most portion of the staple leg and the corner of the staple crown. Accordingly, the staple is dislodged from the surface of the anvil by using the spring ejector to force the staple off of the anvil by its crown.

As noted above, all of the known skin stapler devices utilize similar staple forming and staple release features, namely a spring ejector which releases the staple from the anvil at the crown of the staple. Accordingly, most of these instruments contain a similar number of parts. Thus, most of these known devices are manufactured at around a similar cost with respect to the number of parts utilized in these instruments.

Since skin staplers are generally a disposable, single patient use only device which are intended to be discarded after use in surgery, it is essential that these instruments be provided at the lowest cost possible, i.e. utilize an efficient configuration with minimal parts, without sacrificing quality, safety and functionality. Presently, there is no known skin stapler that provides a multi-directional release mechanism for releasing staples from the instrument after firing without having to utilize a spring ejector to dislodge the staple from the anvil. Additionally, there is no known skin stapler that provides a low featured, cost effective alternative to the skin stapler products identified above.

SUMMARY OF THE INVENTION

The present invention relates to tissue fastening devices which include staples, such as a skin stapler, for closing wounds, incisions or curing a defect in tissue such as fastening a prosthetic to the tissue. The present invention is a surgical stapler which allows for the multi-directional release of staples when fired. The stapler includes a stapler body and a driver contained therein. A magazine is connected to the stapler body and includes a plurality of staples or staple stack. The magazine also includes an anvil having a staple forming surface at a distal end thereof for forming a staple thereon. The anvil is movable from a staple forming position to a staple release position. A feeder element which is spring biased against the plurality of staples is used for feeding each staple to the staple forming surface of the anvil.

A trigger is operatively connected to the driver and is movable from a pre-fire position to a firing position. When actuated, the trigger advances the driver against the staple forming surface of the anvil in order to form the staple. The feeder element is spring biased against the staple stack and advances the staple stack to the staple forming surface upon firing of the stapler.

The trigger is also operatively connected to the anvil for moving the anvil from the staple forming position to the staple release position for releasing or ejecting the staple from the stapler in a multi-directional release manner. Additionally, the trigger is also movable to an intermediate position wherein a lead staple is formed into a box-like configuration prior to being ejected from the stapler upon the trigger being moved to the firing position.

It is an object of the present invention to provide a surgical stapler that allows for the multi-directional release of the staple upon firing.

It is another object of the present invention to provide a surgical stapler that utilizes a movable anvil to release or eject the staple from the stapler in a manner which prevents re-entering of the staple into the instrument and avoids jamming or misfiring.

It is another object of the present invention to provide a surgical stapler that enables the surgeon to fire and advance the stapler in a forward, linear direction away from the surgeon.

It is another object of the present invention to provide a surgical stapler with a multi-directional release mechanism that is cost effective and easy to manufacture and provides a low cost alternative to other known surgical staplers that utilize staple ejection springs.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 7 is a bottom plan view of the actuation trigger of the surgical stapler of FIG. 1;

FIG. 8 is a section view taken along line 8—8 of FIG. 7;

FIG. 9 is a plan view of the preferred movable anvil of FIG. 1; and

FIG. 10 is a side elevation view of the preferred movable anvil of FIG. 1.

DESCRIPTION OF THE PREFERRED EMBODIMENTS

Figure 1:
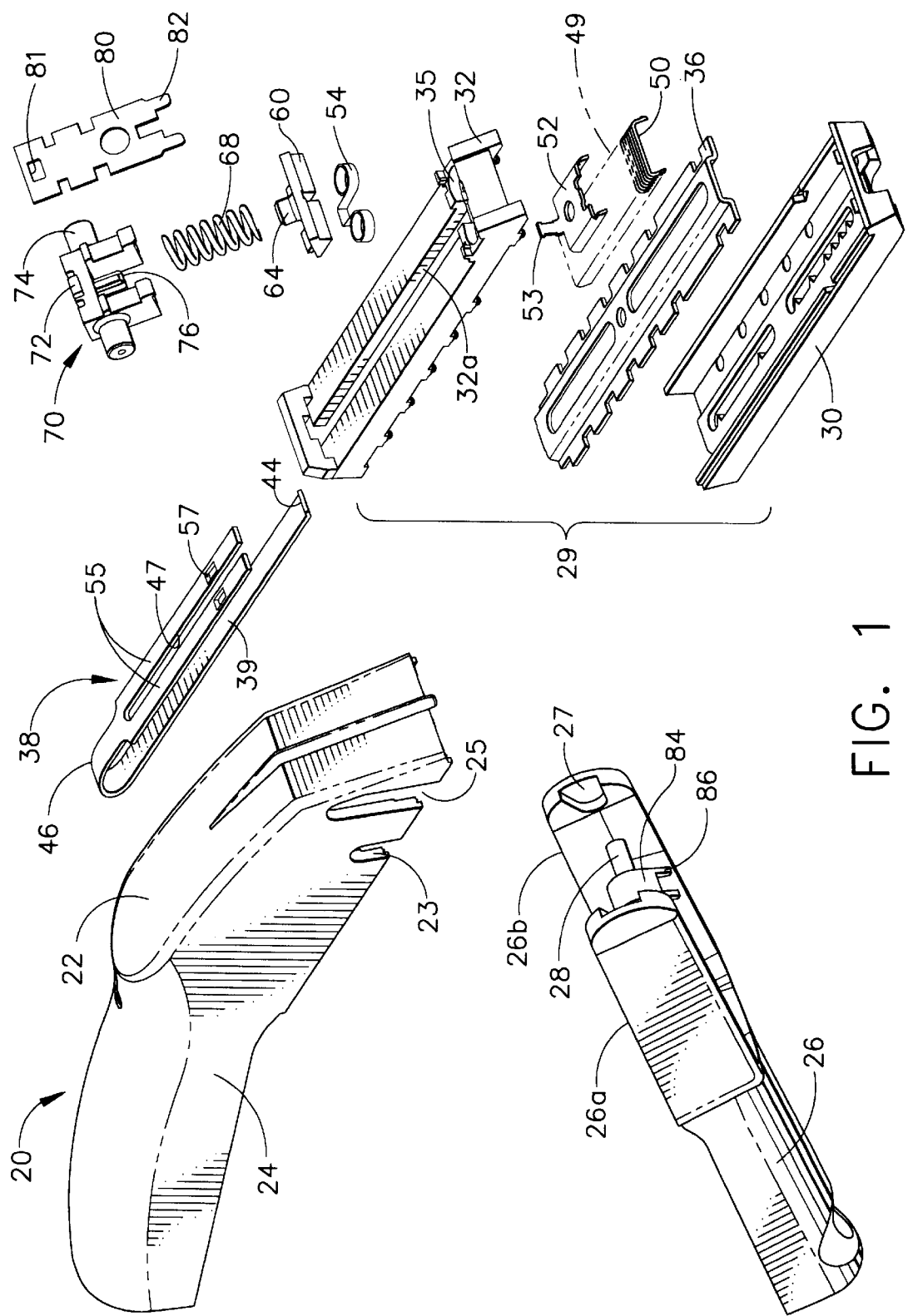
FIG. 1 is an exploded perspective view of a preferred embodiment of an improved surgical stapler employing a movable anvil.

As shown in FIG. 1, the present invention is a tissue fastening device, such as a surgical stapler 20 which is used for the closing of wounds, incisions, defects in tissue or the fastening of a prosthetic to tissue.

The stapler 20 is generally used as a skin stapler for the uses identified above. The stapler 20 comprises a stapler body 22 having an ergonomic handle 24 which is integral with the body 22. A trigger 26 is operatively connected to the body 22 as best illustrated in FIG. 1. Described below are a number of key features of the present invention as best illustrated in FIGS. 1 through 10. However, a more detailed description of these features and functions can be found in U.S. Pat. No. 4,179,057 (Becht et al.) which is incorporated herein by reference. Although not identified by the same name or same reference numeral, a number of features of the stapler 20 according to the present invention are similar in function to those described in U.S. Pat. No. 4,179,057 and are well within the purview of one of ordinary skill in the surgical field.

As best illustrated in FIG. 1, the stapler body 22 includes a pivot bar recess 23 and an actuator recess 25 adjacent each other at the distal end of the stapler body 22. Referring to FIGS. 7 and 8, the actuating trigger 26 includes two arms 26a and 26b which define a substantially Y-shaped configuration for the trigger 26 and is rotatably connected to the stapler body 22. As shown in FIG. 1, a pivot bar 28 is fixed between the trigger arms 26a and 26b and is received in the pivot bar recess 23 of the stapler body 22. Additionally, an anvil pusher 84 having pusher tines 86 is fixed to the pivot bar 28. The trigger arms 26a and 26b also include a trunion recess 27 at the distal end of the arms 26a and 26b.

An actuator 70 includes a driver detent 72 and a trunion 74 located at opposite ends of the actuator 70. The trunions 74 are received in the trunion recess 27 of the trigger arms 26a and 26b. Additionally, the trunions 74 are received in the actuator recess 25 of the stapler body 22. Accordingly, the above-mentioned arrangement, allows for the trigger 26 to be rotated in a direction R from a pre-fire position P (FIG. 3) through an intermediate position I (FIG. 5) to a firing position F (FIG. 6), upon the depression of the trigger 26. When depressed or squeezed by the surgeon, the trigger 26 will be moved or rotated in direction R toward the handle 24 since the trunions 74 of the actuator 70 are movable in the actuator recess 25 of the stapler body 22 and the pivot bar 28 is movable in the pivot bar recess 23 of the stapler body 22.

Referring back to FIG. 1, a driver 80 having a detent aperture 81 located at the proximal end of the driver 80 is connected to the driver detent 72 of the actuator 70. The driver 80 also includes driver tines 82 which are located at the distal end of the driver 80. The actuator 70 includes an upper spring post 76 for receiving a return spring 68. The return spring 68 is also in engagement with a spring seat 60 having a lower spring post 64 for receiving the spring 68 thereon. Accordingly, the return spring 68 is resilientally positioned between the upper spring post 76 of the actuator 70 and the lower spring post 64 of the spring seat 60.

A magazine 29 including a lower magazine section 30 and an upper magazine section 32 is connected to the stapler body 22. The upper magazine section 32 includes a feeder spring recess 35 at the distal end of the upper magazine section 32. The feeder spring recess 35 receives a feeder spring 54 and also supports the spring seat 60. The upper magazine section 32 also includes a longitudinal slot 32a for receiving a feeder shoe lug 53 of a feeder shoe 52. The feeder shoe lug 53 is movable in the slot 32a of the upper magazine section 32 and is movably engaged with the feeder spring 54.

Figure 3:
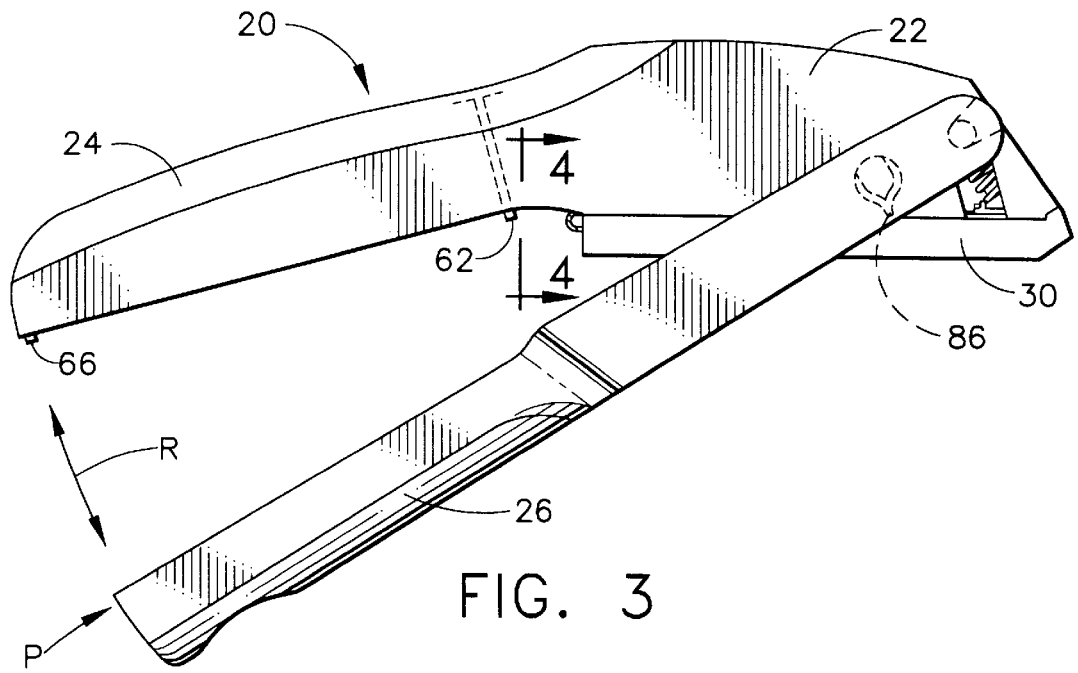
FIG. 3 is a side elevation view of the surgical stapler of FIG. 1 in a pre-fire position.
Figure 3A:
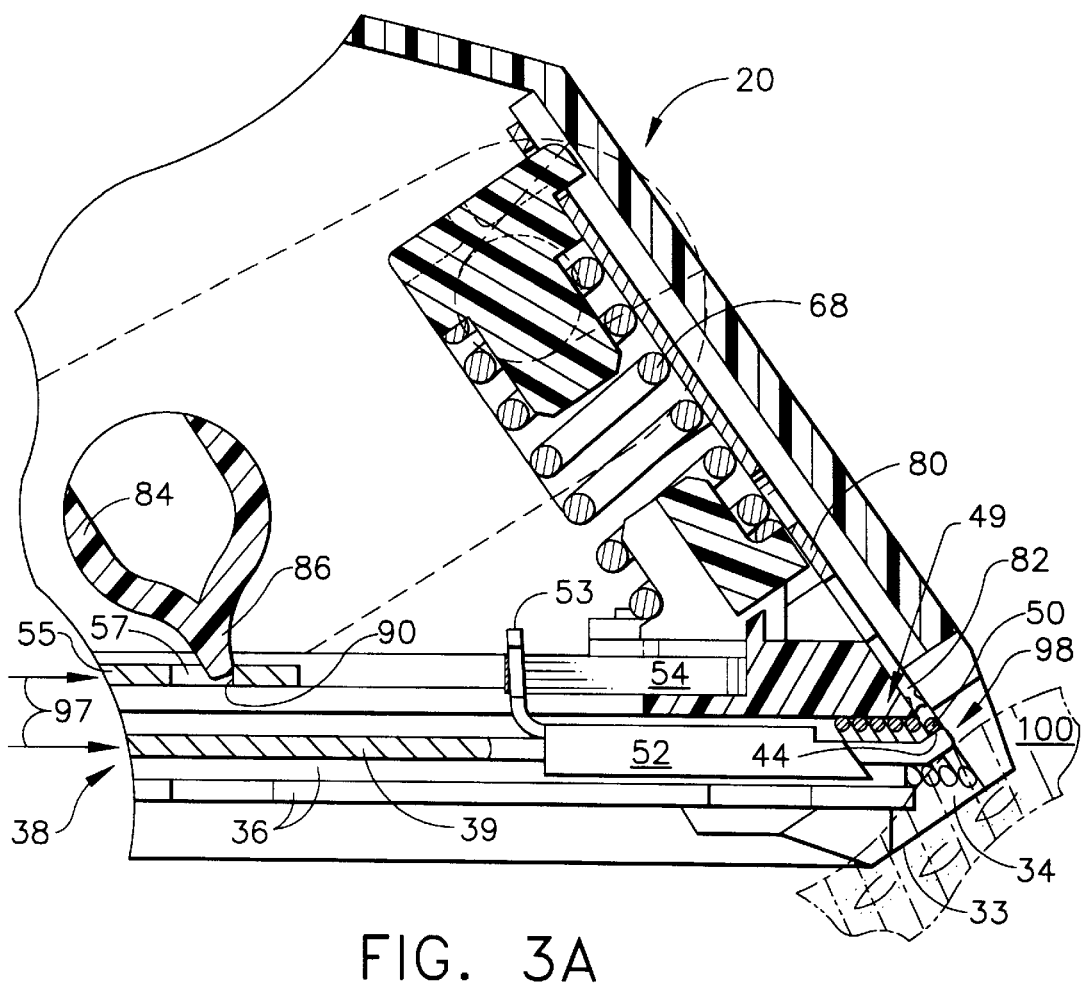
FIG. 3A is a fragmentary and longitudinal section view of the distal portion of the surgical stapler of FIG. 1 in a pre-fire position.

The magazine 29 also includes a staple track 36 for carrying a plurality of staples or a staple stack 49 (FIG. 3A). The staple track 36 is seated within the lower magazine section 30. The feeder shoe 52 is spring biased against the staple stack 49 for urging the staple stack 49 distally along the staple track 36.

As best shown in FIGS. 1, 9 and 10, a movable anvil, generally designated 38, includes an anvil base 39 with a staple forming surface 44 located at a distal end of the anvil base 39 and an anvil return leaf 46 at a proximal end of the anvil base 39. The anvil base 39 is seated on the staple track 36 and assists in carrying the staple stack 49. It is well within the ability of one of ordinary skill in the surgical field to utilize an anvil base 39 that has a wider configuration to provide the sole source for carrying the staple stack 49. Obviously, this would eliminate the need for a separate staple track 36.

Figure 5:
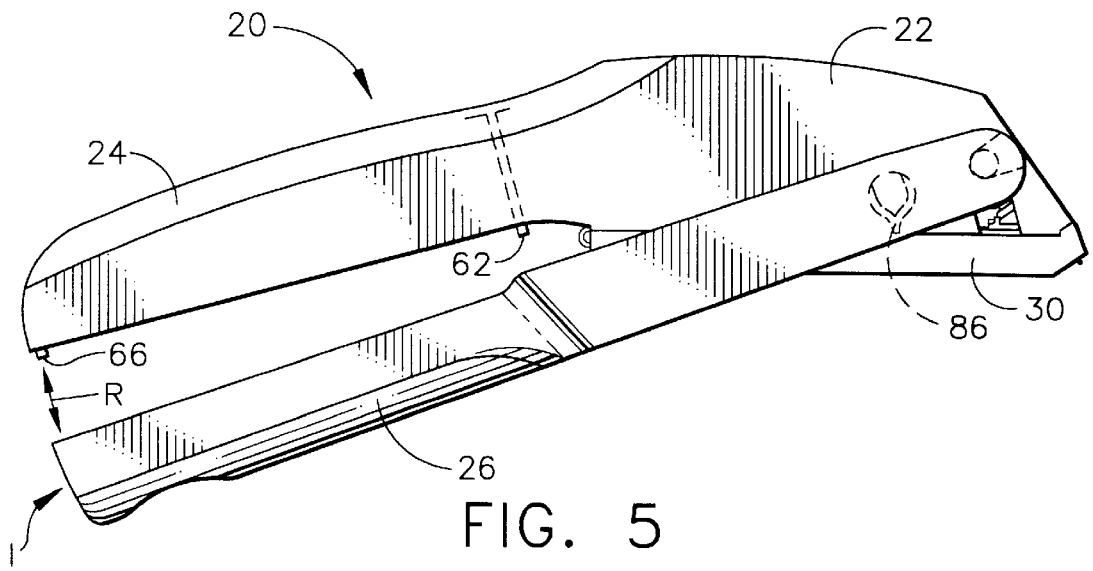
FIG. 5 is a side elevation view of the surgical stapler of FIG. 1 at an intermediate position of trigger actuation where a staple is fully formed.
Figure 5A:
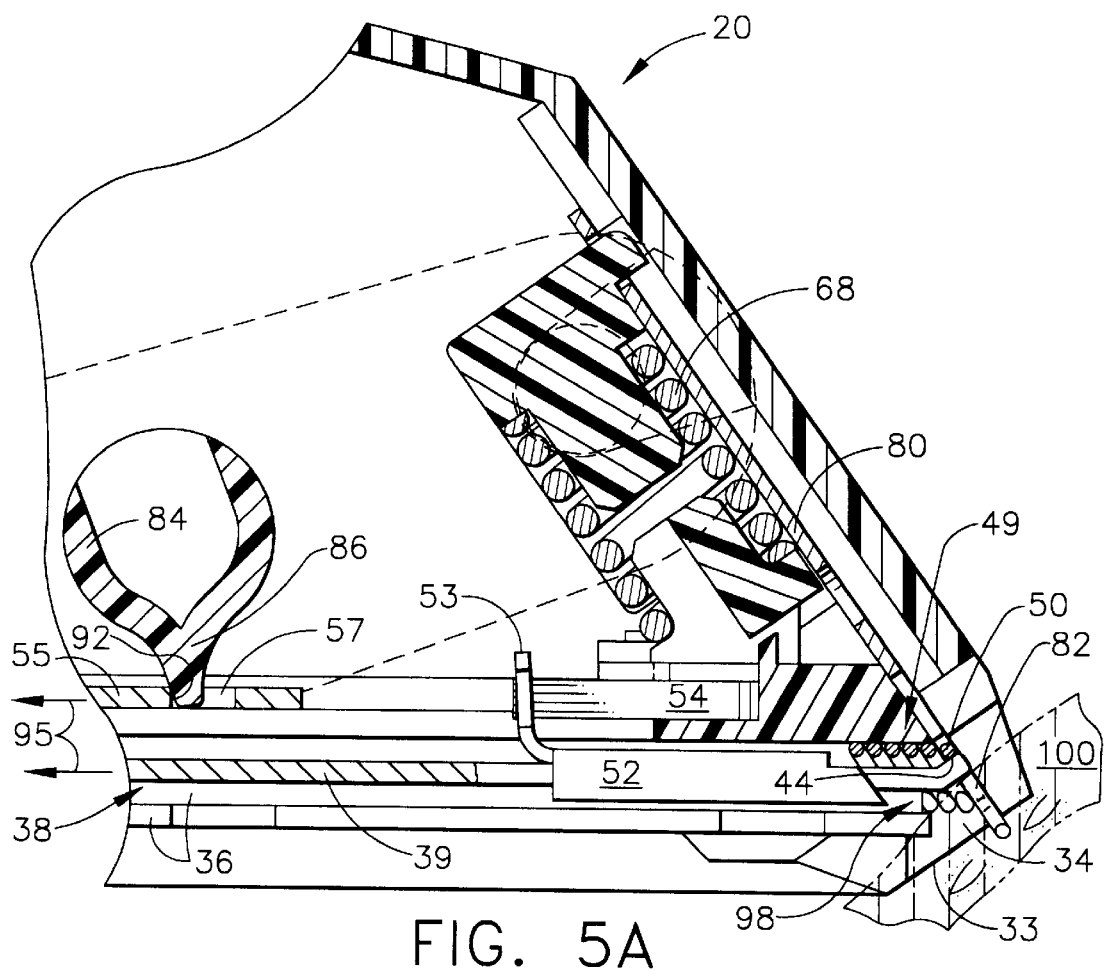
FIG. 5A is a fragmentary and longitudinal section view of the distal portion of the surgical stapler of FIG. 1 wherein the movable anvil is in a staple forming position and is about to be withdrawn from under the fully formed staple.

The staple forming surface 44 is located at the distal-most portion of the anvil base 39 and permits a lead staple 50 from the staple stack 49 to be formed against the staple forming surface 44 when engaged by the driver tines 82 of the driver 80 as best shown in FIGS. 3A and 5A.

Figure 2:
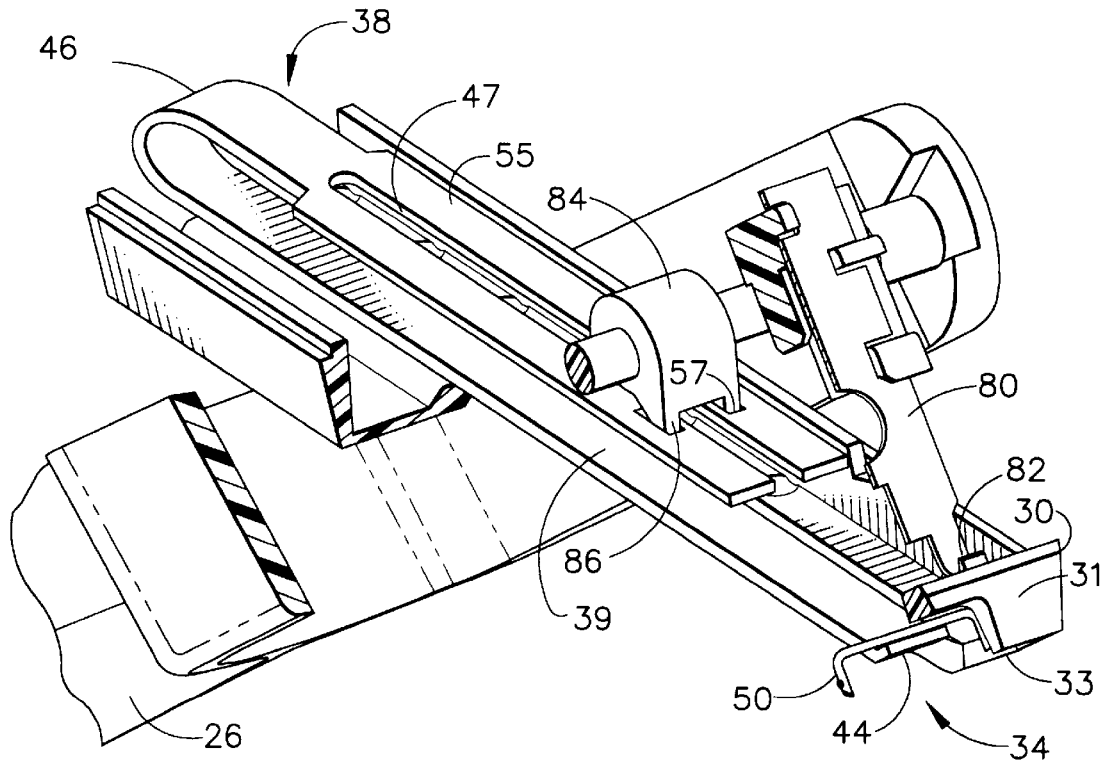
FIG. 2 is a fragmentary and enlarged perspective view of the surgical stapler of FIG. 1 with a portion removed in order to illustrate the working relationship between the movable anvil and an actuation trigger.

The movable anvil also includes a pair of anvil arms 55 fixed to the anvil return leaf 46 and positioned directly above the anvil base 39. The anvil arms 55 are separated from each other and define an anvil longitudinal slot 47 therebetween. Each anvil arm 55 includes an anvil pusher slot 57 located near its distal end. The pusher tines 86 of the anvil pusher 84 are movably positioned in the pusher slots 57 as best shown in FIGS. 2, 3A and 5A.

Additionally, the feeder shoe 52 is movably positioned on the staple track 36 and the anvil base 39. The feeder shoe lug 53 is located in the anvil longitudinal slot 47 between the anvil arms 55 and extends through the upper magazine longitudinal slot 32a.

The feeder shoe 52 is held under tension by the engagement of the feeder shoe lug 53 with the feeder spring 54. This spring-biased arrangement ensures that the staple stack 49 (FIG. 3A) is continuously urged distally along the staple track 36 and the anvil base 39 such that the lead staple 50 is always positioned on the staple forming surface 44 of the movable anvil 38.

Figure 4:
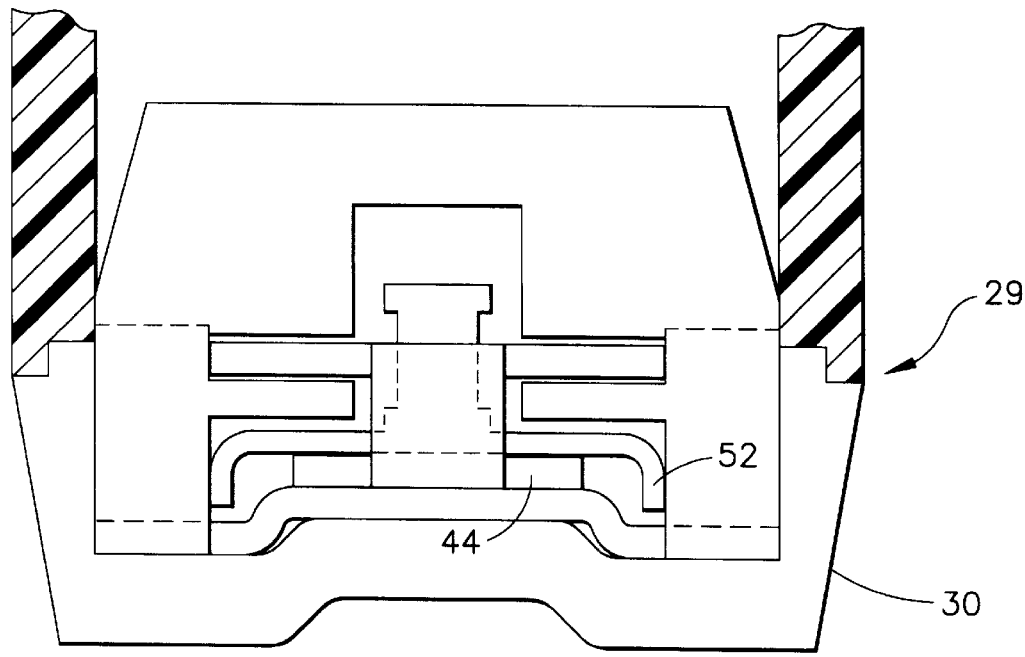
FIG. 4 is a proximal end view of a magazine assembly as taken along line 4—4 of FIG. 3.

The lower magazine section 30 also includes a front face 31 at the distal end of the lower magazine section 30 and a skin contact surface 33 at the under side of the lower magazine section 30 near its distal end as best illustrated in FIG. 4. The front face 31 and the contact surface 33 define an opening 34 at the distal end of the lower magazine section 30. As shown in FIGS. 3A and 5A, the lower magazine section 30 is placed against tissue 100 at the contact surface 33 for permitting the lead staple 50 to be fired and released from the stapler 20.

Figure 6:
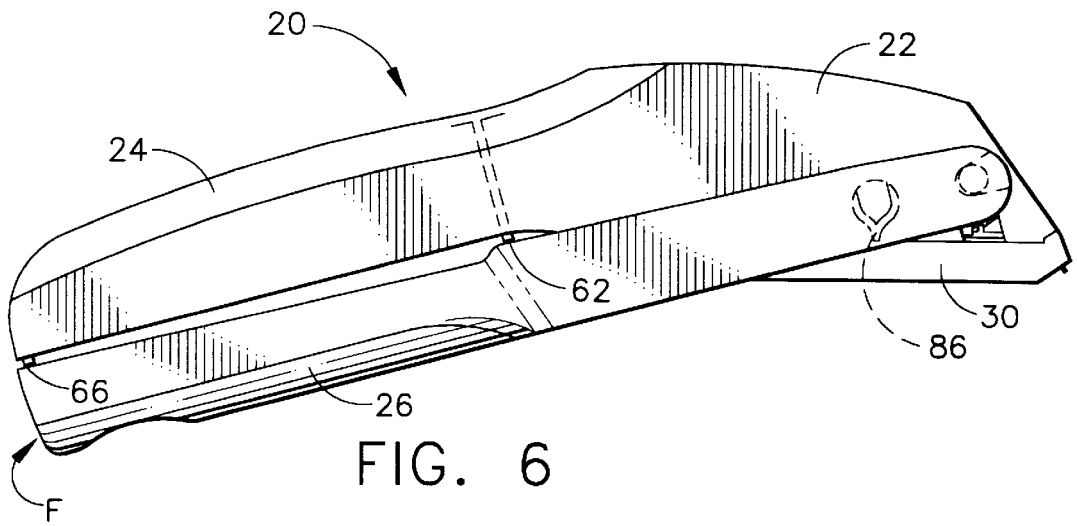
FIG. 6 is a side elevation view of the surgical stapler of FIG. 1 in a firing position.

When in use, the stapler 20 is placed against tissue 100 (FIG. 3A) by placing the contact surface 33 of the lower magazine section 30 directly on the tissue 100 such that the opening 34 of the lower magazine section 30 is located at a position over the tissue 100 where the surgeon desires to place the staple 50. Upon positioning the stapler 20, the surgeon employs a firing sequence using the stapler 20 as best illustrated in FIGS. 3, 5 and 6. FIG. 3A shows the stapler 20 in its pre-fire position P (FIG. 3) wherein the lead staple 50 is positioned on the staple forming surface 44 of the anvil 38. The driver tines 82 of the driver 80 are positioned above the lead staple 50 and are positioned a short distance from the lead staple 50 defining a gap therebetween.

As mentioned above, the pusher tines 86 of the anvil pusher 84 are positioned within the anvil pusher slots 57 of the anvil arms 55. The anvil pusher slots 57 are oversized and permit limited movement of the pusher tines 86 within the pusher slots 57. When the trigger 26 is located at its pre-fire position P (FIG. 3), the pusher tines 86 are located at a distal end 90 of the pusher slots 57. Additionally, when the trigger is in the pre-fire position P, the movable anvil 38 is located in a staple forming position, generally designed 98, e.g. the staple forming surface 44 aligned directly beneath the driver tines 82.

Upon actuation of the trigger 26 along rotation direction R (FIG. 3) to its intermediate position I, (FIG. 5) e.g. the position wherein the lead staple 50 is formed into a box-like configuration, the pusher tines 86 are moved within the pusher slots 57 to a proximal end 92 of the pusher slots 57 as best shown in FIG. 5A.

By further continuing with the firing stroke of the trigger 26 to its firing position F (FIG. 6), the pusher tines 86 are further advanced proximally which causes the movable anvil 38 to be advanced proximally in an anvil movement direction 95, which is a proximal direction, to a staple release position, generally designated 99. The pusher tines 86 force the anvil 38 to move proximally in direction 95 thereby withdrawing the staple forming surface 44 proximally as well. The anvil movement in proximal direction 95 is slight and takes place between the intermediate position I (FIG. 5) and the firing position F (FIG. 6) of the trigger 26 firing stroke. However, the proximal movement of the anvil 38 is sufficient enough for the lead staple 50 to be readily released from the stapler 20 as soon as the staple forming surface 44 is cleared from the lead staple 50. The proximal movement in direction 95 of the staple forming surface 44 permits the lead staple 50 to be ejected from the stapler 20 in a multi-directional release manner. This means that the fired staple 50 will not re-enter the stapler 20 and the stapler 20 can be maneuvered along the tissue 100 in any desired direction. This avoids any possible jamming of the stapler 20. Thus, the surgeon is able to fire and advance the stapler 20 in a forward, linear direction away from the surgeon.

Once the lead staple 50 is ejected, the trigger 26 is permitted to resume its pre-fire position P (FIG. 3) along rotation direction R due to the released compression force exerted on the trigger 26 by the return spring 68. Additionally, the anvil 38 is returned to the staple forming position 98 such that the staple forming surface 44 is aligned directly beneath the driver tines 82 of the driver 80 due to the released compression force moving the pusher tines 86 of the anvil pusher 84 back to the distal end 90 of the pusher slots 57. The anvil 38 is returned to the staple forming position 98 by being moved in a distal direction 97 by the action of the pusher tines 86 acting against the distal end 90 of the pusher slots 57 as best shown in FIG. 3A. Accordingly, as the anvil 38 is returned distally in distal direction 97, the staple stack 49 is advanced distally toward the staple forming surface 44 by feeder shoe 52 in order to position another lead staple 50 on the staple forming surface 44 for conducting another firing of the stapler 20.

Figure 6A:
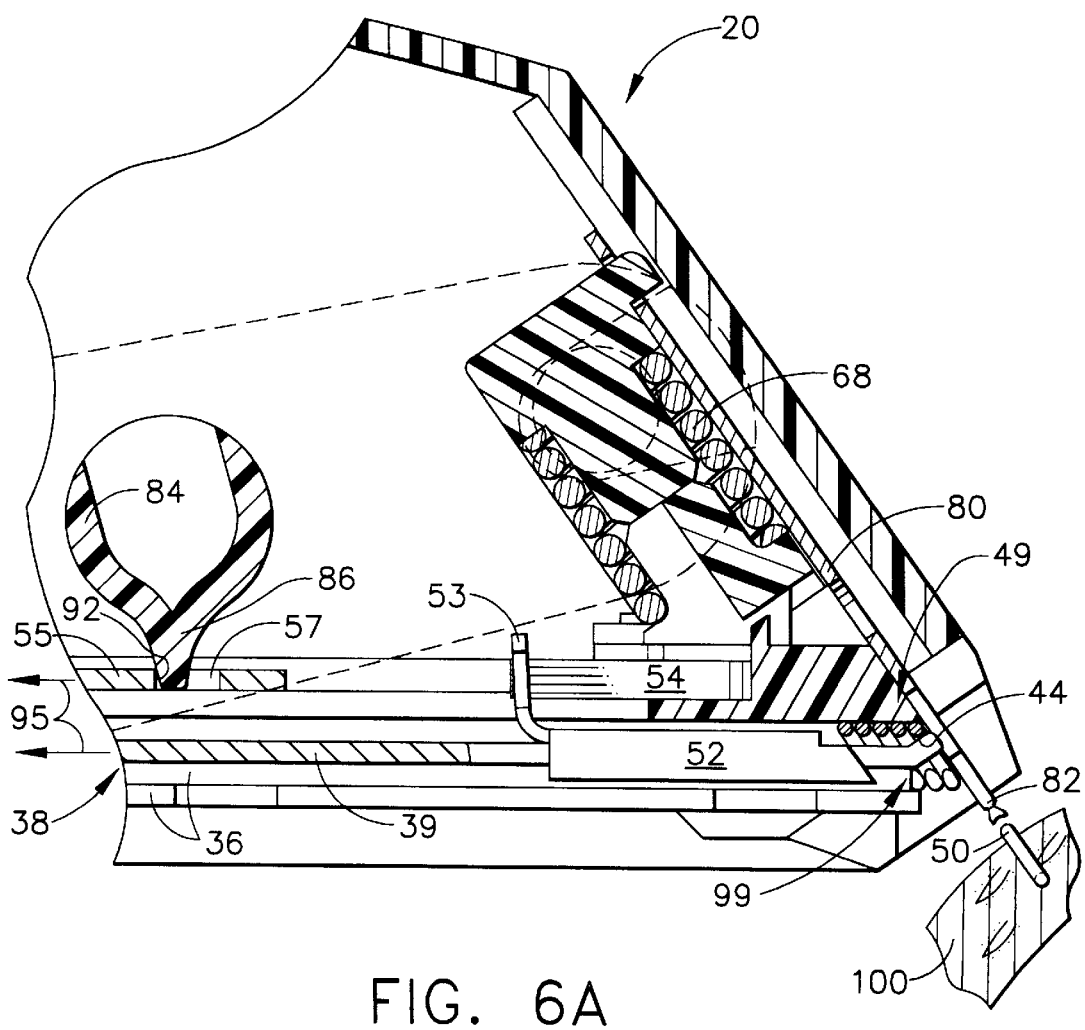
FIG. 6A is a fragmentary and longitudinal section view of the distal portion of the surgical stapler of FIG. 1 in a firing position wherein the movable anvil is in a staple release position.

As best shown in FIGS. 3, 5 and 6, the handle 24 also includes a stop rib 62 fixed to the underside of the handle 24 for contacting the trigger 26 when the trigger 26 is depressed and moved to its firing position F (FIG. 6). The stop rib 62 prevents the trigger 26 from advancing any further once it comes in contact with the stop rib 62. The stop rib 62 eliminates the chance of the driver 80 (FIG. 6A) being driven any further downwardly then desired. Accordingly, the stop rib 62 prevents an overdrive of the driver 80.

Moreover, a trigger stop 66 is also fixed to the underside of the handle 24 at the proximal end of the handle 24 for contacting the proximal end of the trigger 26 when depressed to its firing position F. The trigger stop 66 prevents the trigger 26 from laterally deflecting away from the handle 24.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical stapler comprising:

a stapler body having a driver;

a magazine connected to said stapler body, said magazine including a plurality of staples and an anvil having a staple forming surface at a distal end of said anvil, said anvil being movable from a staple forming position to a staple release position;

a feeder element spring biased against said plurality of staples for feeding each of said staples to said staple forming surface of said anvil; and a trigger operatively connected to said driver for advancing said driver against said anvil so as to form said staple against said staple forming surface of said anvil when said anvil is in said staple forming position, said trigger also being operatively connected to said anvil for moving said anvil from the staple forming position to the staple release position for releasing said staple from said stapler, said trigger being movable from a pre-fire position to an intermediate position and from an intermediate position to a firing position, and wherein said anvil is moved to said staple forming position when said trigger is in said pre-fire position and said anvil is moved to said staple release position when said trigger is in said firing position, said staple being formed in a box-like configuration when said trigger is moved to said intermediate position and said staple being ejected from said stapler when said trigger is moved to said firing position, and wherein said anvil remains in said staple forming position as said staple is formed in said box-like configuration, said anvil moving in a proximal direction to said staple release position after said staple has been formed for permitting said staple to be ejected from said stapler, said anvil including at least one pusher slot and said trigger including at least one pusher tine movably positioned in said at least one pusher slot, said at least one pusher slot being oversized to permit limited movement of said at least one pusher tine within said at least one pusher slot, said limited movement of said at least one tine within said at least one pusher slot occurring as said staple is formed in said box-like configuration.

2. The surgical stapler according to claim 1, wherein said at least one pusher slot has a distal end and said pusher tine contacts said distal end of said at least one pusher slot when said trigger is in the pre-fire position.

3. The surgical stapler according to claim 2, wherein said at least one pusher slot has a proximal end and said at least one pusher tine moves in said at least one pusher slot and contacts said proximal end of said at least one pusher slot when said trigger is moved to the intermediate position.

4. The surgical stapler according to claim 3, wherein said anvil is moved in proximal direction when said trigger is moved to the firing position.

5. The surgical stapler according to claim 4, wherein said anvil is moved in the proximal direction by said at least one pusher tine exerting force against said proximal end of said at least one pusher slot when said trigger is moved to the firing position.

6. The surgical stapler according to claim 5, wherein said anvil is movable in a distal direction to return to said stapler forming position.

7. The surgical stapler according to claim 6, wherein said anvil is moved in the distal direction by said at least one pusher tine exerting force against said distal end of said at least one pusher slot.

8. The surgical stapler according to claim 7, wherein said anvil includes a base and a pair of arms positioned above said base, each arm having a pusher slot therethrough.

9. The surgical stapler according to claim 8, wherein said trigger includes an anvil pusher having a pair of pusher tines.

\* \* \* \* \*